(12) United States Patent
Hilarius et al.

(10) Patent No.: US 7,166,724 B2
(45) Date of Patent: Jan. 23, 2007

(54) IONIC LIQUIDS

(75) Inventors: Volker Hilarius, Gross-Umstadt (DE); Udo Heider, Riedstadt (DE); Michael Schmidt, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 278 days.

(21) Appl. No.: 09/866,926

(22) Filed: May 30, 2001

(65) Prior Publication Data
US 2002/0015883 A1 Feb. 7, 2002

(30) Foreign Application Priority Data
May 30, 2000 (DE) ................ 100 26 565

(51) Int. Cl.
*C07F 5/04* (2006.01)
*C25B 9/10* (2006.01)
*H01G 9/02* (2006.01)
*H01M 6/04* (2006.01)

(52) U.S. Cl. ............ 548/110; 548/343.1; 562/882; 204/242; 252/62.2; 429/188; 429/328

(58) Field of Classification Search .......... 548/343.1, 548/110; 562/882; 204/242; 252/62.2; 429/328, 188; 136/263; 361/503
See application file for complete search history.

(56) References Cited

U.S. PATENT DOCUMENTS 5,827,602 A   10/1998   Koch et al.

FOREIGN PATENT DOCUMENTS

| JP | 11067604 | * | 3/1999 |
|---|---|---|---|
| JP | 11-171981 | * | 6/1999 |
| JP | 11-209583 | * | 8/1999 |
| JP | 2000-17145 | * | 1/2000 |
| JP | 2000-254513 | * | 9/2000 |
| JP | 04311735 | * | 11/2002 |
| WO | WO 98/07729 |  | 2/1998 |

OTHER PUBLICATIONS

Kuhn et al. Feb. 2001 Zeitschrift Fuer Kristallographie- New Crystal Structures, 216(2) 315-317.*
Cismaru et al., Combinations of boric acid with di-and triphenols, Farmacia (1970), 18(9), 531-7.*
Bassett et al., The preparation and properties of some bis(salicylato) borate (III) salts with large cations, Journal of Inorganic and Nuclear Chemistry (1978), 40(6), 987-92.*
Bessler et al, Boron Complexes with dicarboxylic acids: bis(oxalato)borates and bis(malonato)borates, Zeitschrit fuer Naturforschung, Teil B: Anorganische Chemie, Organische Chemie, 37B(8), (1982), pp. 1020-1025.*
Grachek et al., Synthesis and study of new boron complexes, Vestsi Akademii Navuk BSSR, Seryya Khimichnykh Navuk, (1), (1987), 116-18.*
Clegg et al., Salts of the bis(catecholato)borate Anion with Organic Cations, Acta Crystallographica Section C, C54(12), 1998, 1875-1880.*

* cited by examiner

*Primary Examiner*—Joseph K. McKane
*Assistant Examiner*—Rebecca Anderson
(74) *Attorney, Agent, or Firm*—Millen, White, Zelano, Branigan, P.C.

(57) ABSTRACT

An ionic liquid of the formula $K^+A^-$, wherein K and A are as defined herein, can be used in such things as electrochemical cells, supercapacitors, hydraulic liquids, solvents, organic syntheses.

17 Claims, No Drawings

IONIC LIQUIDS

FIELD OF THE INVENTION

The invention relates to ionic liquids for use in electrochemical cells and organic syntheses.

Solvent-free ionic liquids or "salts which are molten at room temperature" were described for the first time in U.S. Pat. No. 2,446,331. The problem with these strong Lewis acids is the formation of toxic gases on contact with atmospheric moisture.

Compounds involving $AlCl_3$ and 1-ethyl-3-methylimidazolium (EMI) chloride have been investigated for a long time. Wilkes and Zaworotko presented novel solvent-free ionic liquids, EMI $BF_4$ and EMI $O_2CCH_3$, in 1992 in J. Chem. Soc., Chem. Commun., p. 965. However, these compounds are unsuitable for use as electrolyte in electrochemical cells since the $BF_4^-$ and $CH_3CO_2^-$ anions are oxidised even at relatively low potentials.

WO 98107729, incorporated herein by reference, describes a new class of conductive salts, the lithium borate complexes. These compounds have shown particularly good results in cycling experiments and have proven particularly stable. The borate salts are in the solid state and thus have relatively low conductivity.

U.S. Pat. No. 5,827,602, incorporated herein by reference, describes the use of ionic liquids from the group consisting of pyridinium, pyridazinium, pyrimidinium, pyrazinium, imidazoleium, pyrazolium, thiazolium, oxazolium and triazolium salts in electrochemical cells. These ionic liquids are particularly suitable for this application owing to good conductivities. The crucial disadvantage consists in the expensive synthesis of the raw materials, in particular the anions.

SUMMARY OF THE INVENTION

An object of the present invention is therefore to provide ionic liquids which have a large liquid range, high thermal stability and low corrosivity and anions which are less expensive to synthesise.

Upon further study of the specification and appended claims, further objects and advantages of this invention will become apparent to those skilled in the art.

These objects are achieved by ionic liquids of the general formula $$K^+A^- \quad (I)$$

in which:

$K^+$ is a cation selected from the group consisting of

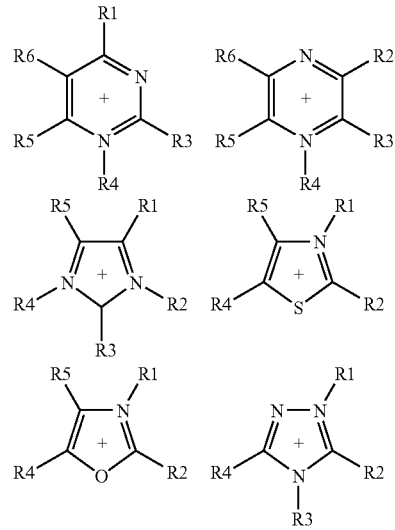

where
- $R^1$ to $R^6$ are identical or different and are each individually
  - H,
  - halogen,
  - an alkyl radical ($C_1$, to $C_8$), which is unsubstituted or partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ where $1<n<6$ and $0<x\leq13$,
  - a phenyl radical which is unsubstituted or partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ where $1<n<6$ and $0<x\leq13$, or
  - one or more pairs of adjacent $R^1$ to $R^6$ can also be an alkylene or alkenylene radical having up to 8 C atoms and which is unsubstituted or partially or fully substituted by further groups, preferably halogen (such as F and Cl), $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ where $1<n<6$ and $0<x\leq13$; and $A^-$ is an anion selected from $$[B(OR^7)_n(OR^8)_m(OR^9)_o(OR^{10})_p]^-$$

where
- $0<n, m, o, p<4$, and $m+n+o+p=4$, and
- $R^7$ to $R^{10}$ are different or identical and are each, individually,
  - an aromatic ring selected from phenyl, naphthyl, anthracenyl and phenanthrenyl, which is unsubstituted or monosubstituted or polysubstituted by $C_nF_{(2n+1-x)}H_x$, where $1<n<6$ and $0<x\leq13$, or halogen (F, Cl or Br),
  - an aromatic heterocyclic ring selected from pyridyl, pyrazyl and pyrimidyl, which is unsubstituted or monosubstituted or polysubstituted by $C_nF_{(2n+1-x)}H_x$, where $1<n<6$ and $0<x\leq13$, or halogen (F, Cl or Br), or
  - an alkyl radical ($C_1$ to $C_8$), which is unsubstituted or partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$, or $C_nF_{(2n+1-x)}H_x$, where $1<n<6$ and $0<x\leq13$; or
- one or more pairs of $R^7$ to $R^{10}$ can also form
  - an aromatic ring selected from phenylene, naphthylene, anthracenylene and phenanthrenylene, which is unsubstituted or monosubstituted or polysubstituted by $C_nF_{(2n+1-x)}H_x$, where 1<n<6 and 0<x≦13, or halogen (F, Cl or Br), an aromatic heterocyclic ring selected from pyridylene, pyrazylene and pyrimidylene, which is unsubstituted or monosubstituted or polysubstituted by $C_nF_{(2n+1-x)}H_x$, where 1<n<6 and 0<x≦13, or halogen (F, Cl or Br), or an alkylene or alkenylene radical having up to 8 C atoms and which is unsubstituted or partially or fully substituted by further groups, preferably halogen (such as F and Cl), $N(C_nF_{(2n+1-x)}H_x)_2$, $O(C_nF_{(2n+1-x)}H_x)$, $SO_2(C_nF_{(2n+1-x)}H_x)$ or $C_nF_{(2n+-x)}H_x$ where 1<n<6 and 0<x≦13; or or $OR^7$ to $OR^{10}$, individually or together, are an aromatic (having, e.g., 6 to 14 C atoms) or aliphatic (having, e.g., 1 to 6 C atoms) carboxyl, dicarboxyl, oxysulfonyl or oxycarbonyl radical, which is unsubstituted or partially or fully substituted by further groups, preferably F, Cl, $N(C_nF_{(2n+1-x)}H_x)_2$, $O(C_nF_{(2n+1-x)}H_x)$, $SO_2(C_nF_{(n+1-x)}H_x)$ or $C_nF_{(2n+1-x)}H_x$, where 1<n<6 and 0<x≦13.

These ionic liquids are suitable as solvents in organic synthesis, but also for use in electrochemical cells. In addition, the ionic liquids are suitable for use in the catalysis of chemical reactions. In addition, they can be used as inert solvents for highly reactive chemicals. A further area is use as hydraulic liquid.

In general, electrochemical cells or batteries comprise a cathode, an anode, a separator and an electrolyte. In general, electrochemical capacitors comprise two electrodes, a separator and an electrolyte. See, e.g., FIGS. 3 and 4 of U.S. Pat. No. 5,827,602.

It has been found that the compounds according to the invention are hydrophobic. Furthermore, the anhydrous synthesis minimises the undesired introduction of water into the system.

Surprisingly, it has been found that the ionic liquids do not corrode, but instead even passivate the aluminium current collector usually used in electrochemical cells. This enables the cycle stability to be increased. In addition, improved thermal stability of the system through the use of ionic liquids has been observed.

It has been found that the addition of solvents of low viscosity enables the conductivity to be improved. Low viscosity together with high conductivity is the prerequisite for use in electrochemical cells. The compounds according to the invention have a large liquid range, making them particularly suitable for these applications.

A prerequisite for use in double layer capacitors is high conductivity. The compounds according to the invention satisfy this criterion. The compounds according to the invention can be employed, alone or in mixtures with other solvents or conductive salts, in electrochemical cells, for the catalysis of chemical reactions or as hydraulic fluids. Suitable solvents are those selected from the group consisting of organic carbonates (for example ethylene carbonate, propylene carbonate and derivatives thereof, butylene carbonate, dimethyl carbonate, diethyl carbonate, methyl ethyl carbonate, etc.), organic carboxylic acid esters (for example γ-butyrolactone, methyl formate, methyl acetate, ethyl acetate, ethyl propionate, methyl propionate, methyl butyrate, ethyl butyrate, etc.), organic carboxylic acid amides (for example dimethylformamide, methylformamide, formamide, etc.), organic ethers (for example 1,2-dimethoxyethane, tetrahydrofuran, 2-methyltetrahydrofuran, tetrahydrofuran derivatives, 1,3-dioxolane, dioxane, dioxolane derivatives, etc.) or other aprotic solvents (for example acetonitrile, sulfolane, dimethyl sulfoxide, nitromethane, phosphoric acid triesters, trimethoxymethane, 3-methyl-2-oxazolidinone, etc.). It is likewise possible to use solvent mixtures, such as, for example, ethylene carbonate/dimethyl carbonate (EC/DMC).

The compounds according to the invention can be used in electrolytes with conventional conductive salts. Examples of suitable electrolytes are those with conductive salts selected from $LiPF_6$, $LiBF_4$, $LiClO_4$, $LiAsF_6$, $LiCF_3SO_3$, $LiN(CF_3SO_2)_2$ and $LiC(CF_3SO_2)_3$, and mixtures thereof. The electrolytes may also comprise organic isocyanates (DE 199 44 603) for reducing the water content.

Lithium complex salts of the following formula (DE 199 32 317) can also be present in the electrolyte composition

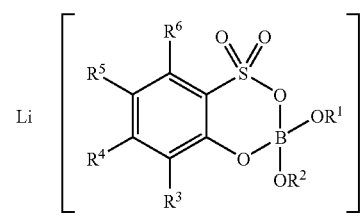

where $R^1$ and $R^2$ are identical or different, are optionally bonded directly to one another via a single or double bond, and are each, individually or together, an aromatic ring from the group consisting of phenyl, naphthyl, anthracenyl and phenanthrenyl, which may be unsubstituted or mono- to hexasubstituted by alkyl ($C_1$ to $C_6$), alkoxy groups ($C_1$ to $C_6$) or halogen (F, Cl or Br), or are each, individually or together, an aromatic heterocyclic ring from the group consisting of pyridyl, pyrazyl and pyrimidyl, which may be unsubstituted or mono- to tetrasubstituted by alkyl ($C_1$ to $C_6$), alkoxy groups ($C_1$ to $C_6$) or halogen (F, Cl or Br), or are each, individually or together, an aromatic ring from the group consisting of hydroxybenzocarboxyl, hydroxynaphthalenecarboxyl, hydroxybenzosulfonyl and hydroxynaphthalenesulfonyl, which may be unsubstituted or mono- to tetrasubstituted by alkyl ($C_1$ to $C_6$), alkoxy groups ($C_1$ to $C_6$) or halogen (F, Cl or Br), $R^3$–$R^6$ may each, individually or in pairs and optionally bonded directly to one another by a single or double bond, have the following meanings:

1. alkyl ($C_1$ to C6), alkoxy (C1 to C6) or halogen (F, Cl or Br)
2. an aromatic ring from the groups phenyl, naphthyl, anthracenyl and phenanthrenyl, which may be unsubstituted or mono- to hexasubstituted by alkyl ($C_1$ to $C_6$), alkoxy groups ($C_1$ to $C_6$) or halogen (F, Cl or Br), pyridyl, pyrazyl and pyrimidyl, which may be unsubstituted or mono- to tetrasubstituted by alkyl ($C_1$ to $C_6$), alkoxy groups ($C_1$ to $C_6$) or halogen (F, Cl or Br).

These compounds can be prepared by the following process (DE 199 32 317):

a) chlorosulfonic acid is added to 3-, 4-, 5- or 6-substituted phenol in a suitable solvent,
b) the intermediate from a) is reacted with chlorotrimethylsilane, and the reaction mixture is filtered and subjected to fractional distillation.
c) the intermediate from b) is reacted with, for example, lithium tetramethoxyborate(1-) in a suitable solvent, and the end product is isolated therefrom.

The electrolytes may likewise comprise compounds of the following formula (DE 199 41 566):

$$[((R^1(CR^2R^3)_k)_lA_x)_yKt]^+ N(CF_3)_2$$

where

Kt=N, P, As, Sb, S or Se
A=N, P, P(O), O, S, S(O), SO$_2$, As, As(O), Sb or Sb(O)
R$^1$, R$^2$ and R$^3$ are identical or different and are
H, halogen, substituted and/or unsubstituted alkyl $C_nH_{2n+1}$, substituted and/or unsubstituted alkenyl having 1–18 carbon atoms and one or more double bonds, substituted and/or unsubstituted alkynyl having 1–18 carbon atoms and one or more triple bonds, substituted and/or unsubstituted cycloalkyl $C_mH_{2m-1}$, mono- or polysubstituted and/or unsubstituted phenyl, or substituted and/or unsubstituted heteroaryl,
A may be included in R$^1$, R$^2$ and/or R$^3$ in various positions,
Kt may be included in a cyclic or heterocyclic ring,
the groups bonded to Kt may be identical or different, where n=1–18
m=3–7
k=0 or 1–6
l=1 or 2 in the case where x=1 and 1 in the case where x=0
x=0 or 1
y=1–4.

The process for the preparation of these compounds is characterised in that an alkali metal salt of the general formula $$D^+ N(CF_3)_2$$

where D$^+$ is selected from the group of alkali metals, is reacted, in a polar organic solvent, with a salt of the general formula $$[((R^1(CR^2R^3)_k)_lA_x)_yKt]^+ E$$

where

Kt, A, R$^1$, R$^2$, R$^3$, k, l, x and y are as defined above, and
$^-$E is F$^-$, Cl$^-$, Br$^-$, I$^-$, BF$_4^-$, ClO$_4^-$, AsF$_6^-$, SbF$_6^-$ or PF$_6^-$.

However, use can also be made of electrolytes comprising compounds of the general formula (DE 199 53 638)

$$X—(CYZ)_m—SO_2N(CR^1R^2R^3)_2$$

where

X is H, F, Cl, $C_nF_{2n+1}$, $C_nF_{2n-1}$ or $(SO_2)_kN(CR^1R^2R^3)_2$
Y is H, F or Cl
Z is H, F or Cl
R$^1$, R$^2$ and R$^3$ are H and/or alkyl, fluoroalkyl or cycloalkyl having up to 9 C atoms
m is 0–9 and, if X=H, m≠0
n is 1–9
k is 0 if m=0 and k=1 if m=1–9, These compounds can be prepared by reacting partially or perfluorinated alkylsulfonyl fluorides with dimethylamine in organic solvents.

Use can also be made of electrolytes comprising complex salts of the general formula (DE 199 51 804)

$$M^{x+}[EZ]_{x/y}^{y-}$$

in which:

x and y are 1,2,3,4,5 or 6
M$^{x+}$ is a metal ion
E is a Lewis acid selected from the group
BR$^1$R$^2$R$^3$, AlR$^1$R$^2$R$^3$, PR$^1$R$^2$R$^3$R$^4$R$^5$, AsR$^1$R$^2$R$^3$R$^4$R$^5$ and VR$^1$R$^2$R$^3$R$^4$R$^5$, R$^1$ to R$^5$ are identical or different, are optionally bonded directly to one another by a single or double bond, and each, individually or together, are
a halogen (F, Cl or Br),
an alkyl or alkoxy radical (C$_1$ to C$_8$), which may be partially or fully substituted by F, Cl or Br,
an aromatic ring, optionally bonded via oxygen, selected from the group phenyl, naphthyl, anthracenyl and phenanthrenyl, which may be unsubstituted or mono- to hexasubstituted by alkyl (C$_1$ to C$_8$) or F, Cl or Br,
an aromatic heterocyclic ring, optionally bonded via oxygen, selected from the group pyridyl, pyrazyl and pyrimidyl, which may be unsubstituted or mono- to tetrasubstituted by alkyl (C$_1$ to C$_8$) or F, Cl or Br, and
Z is OR$^6$, NR$^6$R$^7$, CR$^6$R$^7$R$^8$, OSO$_2$R$^6$, N(SO$_2$R$^6$)(SO$_2$R$^7$), C(SO$_2$R$^6$)(SO$_2$R$^7$)(SO$_2$R$^8$) or OCOR$^6$, where
R$^6$ to R$^8$ are identical or different, are optionally bonded directly to one another by a single or double bond and are each, individually or together,
hydrogen or as defined for R$^1$ to R$^5$.

These compounds can be prepared by reacting a corresponding boron or phosphorus Lewis acid/solvent adduct with a lithium or tetra-alkylammonium imide, methanide or triflate.

The electrolyte composition can also contain borate salts (DE 199 59 772) of the general formula

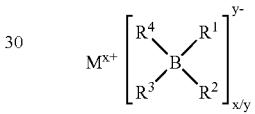

in which:

M is a metal ion or tetraalkylammonium ion,
x and y are 1, 2, 3, 4, 5 or 6,
R$^1$ to R$^4$ are identical or different and are alkoxy or carboxyl radicals (C$_1$–C$_8$), which are optionally bonded directly to one another by a single or double bond.

These borate salts are prepared by reacting lithium tetraalkoxyborate or a 1:1 mixture of lithium alkoxide with a borate with a suitable hydroxyl or carboxyl compound in a ratio of 2:1 or 4:1 in an aprotic solvent.

The compounds according to the invention may also be employed in electrolytes comprising lithium fluoroalkylphosphates of the general formula $$Li^+[PF_x(C_yF_{2y+1-z}H_z)_{6-x}]^-$$

in which

1≦x≦5
3≦y≦8
0≦z≦2y+1 and the ligands (C$_y$F$_{2y+1-z}$H$_z$) may be identical or different, with the exception of the compounds of the general formula $$Li^+[PF_a(CH_bF_c(CF_3)_d)_e]^-$$

in which a is an integer from 2 to 5, b=0 or 1, c=0 or 1, d=2 and e is an integer from 1 to 4, with the provisos that b and c are not simultaneously each=0, and the sum a+e is equal to 6, and the ligands (CH$_b$F$_c$(CF$_3$)$_d$) may be identical or different (DE 100 089 55). The process for the preparation of lithium fluoroalkylphosphates of the above-mentioned formula is characterised in that at least one compound of the general formula $H_mP(C_nH_{2n+1})_{3-m}$, $OP(C_nH_{2n+1})_3$, $Cl_mP(C_nH_{2n+1})_{3-m}$, $F_mP(C_nH_{2n+1})_{3-m}$, $Cl_oP(C_nH_{2n+1})_{5-o}$, $F_oP(C_nH_{2n+1})_{5-o}$, in each of which
$0 \leq m \leq 2$, $3 \leq n \leq 8$ and $0 \leq o \leq 4$, is fluorinated by electrolysis in hydrogen fluoride, the resultant mixture of fluorination products is separated by extraction, phase separation and/or distillation, and the resultant fluorinated alkyl-phosphorane is reacted with lithium fluoride in an aprotic solvent mixture with exclusion of moisture, and the resultant salt is purified and isolated by conventional methods.

The compounds according to the invention can be employed in electrolytes for electrochemical cells which contain positive-electrode material of coated metal cores selected from the group of Sb, Bi, Cd, In, Pb, Ga and tin or alloys thereof (DE 100 16 024). The process for the production of this positive-electrode material is characterised in that
a) a suspension or sol of the metal or alloy core in urotropin is prepared,
b) the suspension is emulsified with $C_5$–$C_{12}$-hydrocarbons,
c) the emulsion is precipitated onto the metal or alloy cores, and
d) the metal hydroxides or oxyhydrides are converted into the corresponding oxide by heat-treatment of the system.

The compounds according to the invention can also be employed in electrolytes for electrochemical cells having negative electrodes made from common lithium intercalation and insertion compounds, but also with negative-electrode materials made of lithium mixed oxide particles coated with one or more metal oxides (DE 199 22 522) by suspending the particles in an organic solvent, adding a solution of a hydrolysable metal compound and a hydrolysis solution to the suspension, and then filtering off, drying and optionally calcining the coated particles. They can also made of lithium mixed oxide particles coated with one or more polymers (DE 199 46 066), obtained by a process in which the particles are suspended in a solvent, and the coated particles are subsequently filtered off, dried and optionally calcined. The compounds according to the invention may likewise be employed in systems having negative electrodes made of lithium mixed oxide particles with one or more coatings of alkali metal compounds and metal oxides (DE 100 14 884). The process for the production of these materials is characterised in that the particles are suspended in an organic solvent, an alkali metal salt compound suspended in an organic solvent is added, metal oxides dissolved in an organic solvent are added, a hydrolysis solution is added to the suspension, and the coated particles are subsequently filtered off, dried and calcined.

A general example of the invention is explained in greater detail below.

In order to prepare the anion selected from the group

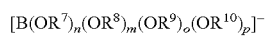
$[B(OR^7)_n(OR^8)_m(OR^9)_o(OR^{10})_p]^-$ where
$0 \leq n, m, o, p \leq 4$, and $m+n+o+p=4$, and $R^7$ to $R^{10}$ are different or identical and are each, individually, an aromatic ring selected from phenyl, naphthyl, anthracenyl and phenanthrenyl, which is unsubstituted or monosubstituted or polysubstituted by $C_nF_{(2n+1-x)}H_x$, where $1<n<6$ and $0<x \leq 13$, or halogen (F, Cl or Br), an aromatic heterocyclic ring selected from pyridyl, pyrazyl and pyrimidyl, which is unsubstituted or monosubstituted or polysubstituted by $C_nF_{(2n+1-x)}H_x$, where $1<n<6$ and $0<x \leq 13$, or halogen (F, Cl or Br), or an alkyl radical ($C_1$ to $C_8$), which is unsubstituted or partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$, or $C_nF_{(2n+1-x)}H_x$, where $1<n<6$ and $0<x \leq 13$; or one or more pairs of $R^7$ to $R^{10}$ can also form an aromatic ring selected from phenylene, naphthylene, anthracenylene and phenanthrenylene, which is unsubstituted or monosubstituted or polysubstituted by $C_nF_{(2n+1-x)}H_x$, where $1<n<6$ and $0<x \leq 13$, or halogen (F, Cl or Br), an aromatic heterocyclic ring selected from pyridylene, pyrazylene and pyrimidylene, which is unsubstituted or monosubstituted or polysubstituted by $C_nF_{(2n+1-x)}H_x$, where $1<n<6$ and $0<x \leq 13$, or halogen (F, Cl or Br), or an alkylene or alkenylene radical having up to 8 C atoms and which is unsubstituted or partially or fully substituted by further groups, preferably halogen (such as F and Cl), $N(C_nF_{(2n+1-x)}H_x)_2$, $O(C_nF_{(2n+1-x)}H_x)$, $SO_2(C_nF_{(n+1-x)}H_x)$ or $C_nF_{(2n+1-x)}H_x$ where $1<n<6$ and $0<x \leq 13$; or or $OR^7$ to $OR^{10}$, individually or together, are an aromatic (having, e.g., 6 to 14 C atoms) or aliphatic (having, e.g., 1 to 6 C atoms) carboxyl, dicarboxyl, oxysulfonyl or oxycarbonyl radical, which is unsubstituted or partially or fully substituted by further groups, preferably F, Cl, $N(C_nF_{(2n+1-x)}H_x)_2$, $O(C_nF_{(2n+1-x)}H_x)$ $SO_2(C_nF_{(2n+1-x)}H_x)$ or $C_nF_{(2n+1-x)}H_x$, where $1<n<6$ and $0<x \leq 13$, a known process from WO 98/07729 is used.

In order to prepare the cation selected from the group consisting of

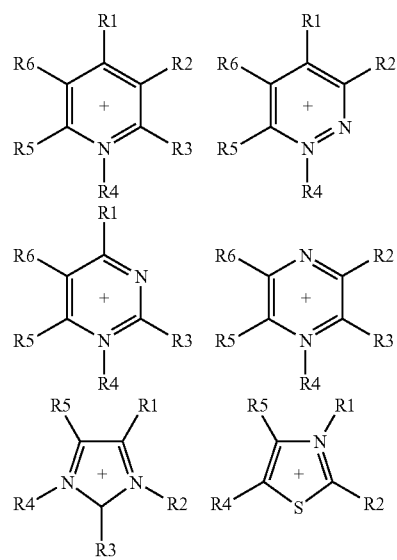

-continued

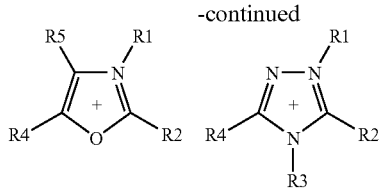

a known process from U.S. Pat. No. 5,827,602 is used. The starting materials are reacted for from about 0.5 to 12 hours, preferably 1–4 hours, in an aprotic organic solvent, at temperatures in the liquid range of the solvent.

In order to remove the by-products, the mixture is cooled to as far as −30° C., for example to from −10° C. to −20° C. in the case of LiCl as by-product, and the by-product which precipitates out is filtered off, preferably filtered off by vacuum.

The solvent/product mixture can be employed directly in the electrolyte. If desired, the solvent can also be distilled off and the resultant product dried.

The examples below are intended to explain the invention in greater detail, but without representing a limitation.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 100 26 565.0 filed May 30, 2000 is hereby incorporated by reference.

EXAMPLES

Example 1

Synthesis of 1-ethyl-3-methylimidazolium bis[1,2-benzenediolato-O,O']borate

Lithium bis[1,2-benzenediolato-O,O']borate is synthesised in accordance with WO 94/27335 or WO 98/07729. The product is reacted in acetonitrile in accordance with the following reaction equation:

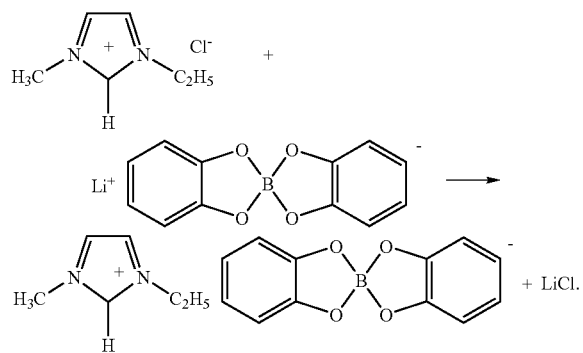

The reaction mixture is filtered by vacuum through a glass frit with cooling in order to remove the LiCl formed as by-product. The solvent is distilled off under reduced pressure, and the resultant 1-ethyl-3-methylimidazolium bis[1,2-benzenediolato-O,O']borate is dried under reduced pressure.

Example 2

Synthesis of 1-ethyl-3-methylimidazolium bis[salicylato]borate

Lithium bis[salicylato]borate is synthesised in accordance with WO 94/27335 or in accordance with WO 98/07729 and reacted with 1-ethyl-2-methylimidazolium chloride in acetonitrile. The reaction mixture is filtered by vacuum through a glass frit with cooling in order to remove the LiCl formed as by-product. The solvent is distilled off under reduced pressure, and the resultant 1-ethyl-3-methyl-imidazolium bis[salicylato]borate is dried under reduced pressure.

Example 3

Synthesis of 1-ethyl-3-methylimidazolium bis[oxalato]borate

Lithium bis[oxalato]borate is synthesised in accordance with WO 94/27335 or in accordance with WO 98/07729 and reacted with 1-ethyl-2-methylimidazolium chloride in acetonitrile. The reaction mixture is filtered by vacuum through a glass frit with cooling in order to remove the LiCl formed as by-product. The solvent is distilled off under reduced pressure, and the resultant 1-ethyl-3-methyl-imidazolium bis[oxalato]borate is dried under reduced pressure.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of the general formula $$K^+ A^- \qquad (I)$$

wherein:

$K^+$ is a cation selected from:

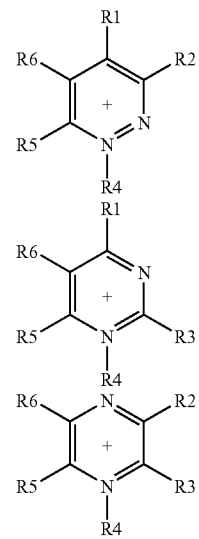

-continued

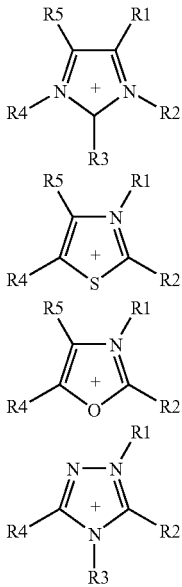

wherein

R¹ to R⁶ are identical or different and are each individually H, a halogen, an alkyl radical ($C_1$ to $C_8$), which is unsubstituted, or which is partially or fully substituted by F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$, wherein $1<n<6$ and $0<x\leq 13$ a phenyl radical which is unsubstituted or which is partially or fully substituted by F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ wherein $1<n<6$ and $0<x\leq 13$, or one or more pairs of adjacent R¹ to R⁶ can also be an alkylene or alkenylene radical and having up to 8 C atoms, wherein the radical is unsubstituted or partially or fully substituted by halogen, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ wherein $1<n<6$ and $0<x\leq 13$ wherein A⁻ is an anion selected from

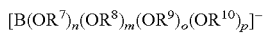

wherein $0\leq n, m, o, p \leq 4$, and $m+n+o+p=4$, and

R⁷ to R¹⁰ are different or identical and are each, individually:

an aromatic ring selected from a phenyl, naphthyl, anthracenyl and phenanthrenyl ring, which is unsubstituted, or which is monosubstituted or polysubstituted by $C_nF_{(2n+1-x)}H_x$, wherein $1<n<6$ and $0<x\leq 13$, or halogen, or an aromatic heterocyclic ring selected from a pyridyl, pyrazyl and pyrimidyl ring, which is unsubstituted, or which is mono-substituted or polysubstituted by $C_nF_{(2n+1-x)}H_x$, wherein $1<n<6$ and $0<x\leq 13$, or halogen, and wherein one or more pairs of R⁷ to R¹⁰ can also form an aromatic ring selected from a anthracenylene and phenanthrenylene ring, which is unsubstituted or an aromatic ring selected from a phenylene, naphthylene, anthracenylene and phenanthrenyl ring which is monosubstituted or polysubstituted by $C_nF_{(2n+1-x)}H_x$, wherein $1<n<6$ and $0<x\leq 13$, or halogen, an aromatic heterocyclic ring selected from a pyridylene, pyrazylene and pyrimidylene ring, which is unsubstituted, or which is mono-substituted or polysubstituted by $C_nF_{(2n+1-x)}H_x$, wherein $1<n<6$ and $0<x\leq 13$, or halogen, or OR⁷ to OR¹⁰, individually or together, are aliphatic having 1 to 6 C atoms and which is a carboxyl, dicarboxyl, oxysulfonyl or oxycarbonyl radical, which is unsubstituted, or which is partially or fully substituted by F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$, wherein $1<n<6$ and $0<x\leq 13$.

2. A compound according to claim 1, wherein at least one of R¹ to R⁶ of the cation is an alkyl radical which is unsubstituted or partially or fully substituted by F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ wherein $1<n<6$ and $0<x\leq 13$.

3. A compound according to claim 1, wherein at least one of R¹ to R⁶ of the cation is a phenyl radical which is unsubstituted or partially or fully substituted by F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ wherein $1<n<6$ and $0<x\leq 13$.

4. A compound according to claim 1, wherein at least a pair of R¹ to R⁶ of the cation is an alkylene or alkenylene radical which is unsubstituted or partially or fully substituted by halogen, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ wherein $1<n<6$ and $0<x\leq 13$.

5. A compound according to claim 1, wherein at least one of R⁷ to R¹⁰ of the anion is an aromatic ring selected from a phenyl, anthracenyl and phenanthrenyl ring, which is unsubstituted, or which is monosubstituted or polysubstituted by $C_nF_{(2n+1-x)}H_x$, wherein $1<n<6$ and $0<x\leq 13$, or by a halogen.

6. A compound according to claim 1, wherein at least one of R⁷ to R¹⁰ of the anion is an aromatic heterocyclic ring selected from a pyridyl, pyrazyl and pyrimidyl ring, which is unsubstituted, or which is monosubstituted or polysubstituted by $C_nF_{(2n+1-x)}H_x$, wherein $1<n<6$ and $0<x\leq 13$, or F, Cl or Br.

7. A compound according to claim 1, wherein at least one pair of R⁷ to R¹⁰ of the anion is an aromatic ring selected from an anthracenylene and phenanthrenylene ring, which is unsubstituted or a phenylene, naphthylene anthracenylene and phenanthrenyl ring, which is monosubstituted or polysubstituted by $C_nF_{(2n+1-x)}H_x$, wherein $1<n<6$ and $0<x\leq 13$, or halogen.

8. A compound according to claim 1, wherein at least one pair of R⁷ to R¹⁰ of the anion is an aromatic heterocyclic ring selected from a pyridylene, pyrazylene and pyrimidylene ring, which is unsubstituted, or which is mono-substituted or polysubstituted by $C_nF_{(2n+1-x)}H_x$, wherein $1<n<6$ and $0<x\leq 13$, or by halogen.

9. An electrochemical cell comprising a cathode, an anode, a separator, and the ionic liquid of claim 1.

10. A supercapacitor comprised of at least a pair of electrodes, a separator, and the ionic liquid of claim 1.

11. An electrolyte composition comprising an ionic liquid of claim 1 and an aprotic solvent.

12. An electrolyte composition comprising an ionic liquid of claim 1 and a conductive salt.

13. A method for making a compound according to claim 1, comprising reacting a chloride salt of the formula K⁺Cl⁻ with a lithium salt of the formula Li⁺A⁻ within an aprotic solvent.

14. A compound selected from:

1-ethyl-3-methylimidazolium bis[1,2-benzenediolato-O, O']borate, 1-ethyl-3-methylimidazolium bis[oxalato]borate, and 1-ethyl-3-methylimidazolium bis[salicylato]borate.

15. A compound according to claim 14, wherein said compound is:

1-ethyl-3-methyl imidazolium bis [1,2-benzenediolato-O, O']borate.

16. A compound according to claim 14, wherein said compound is:

1-ethyl-3-methylimidazolium bis[oxalato]borate.

17. A compound according to claim 1, wherein $OR^7$ to $OR^{10}$, individually or together, are aliphatic having 1 to 6 C atoms and which is a carboxyl, dicarboxyl, oxysulfonyl or oxycarbonyl radical, which is unsubstituted, or which is partially or fully substituted by F, Cl, $N(C_nF_{(2n+1-x)}H_x)_2$, $O(C_nF_{(2n+1-x)}H_x)$, $SO_2(C_nF_{(2n+-x)}H_x)$ or $C_nF_{(2n+1-x)}H_x$, wherein $1<n<6$ and $0<x\leq13$.

* * * * *

UNITED STATES PATENT AND TRADEMARK OFFICE
CERTIFICATE OF CORRECTION

PATENT NO.       : 7,166,724 B2
APPLICATION NO.  : 09/866926
DATED            : January 23, 2007
INVENTOR(S)      : Volker Hilarius It is certified that error appears in the above-identified patent and that said Letters Patent is hereby corrected as shown below:

Column 11, line 39, reads "and having" should read -- having --
Column 11, line 43, reads "or $C_n F$" should read -- or $C_n F$ --

Column 11, line 62, reads "from a anthracenylene" should read -- from an anthracenylene --
Column 13, line 3, reads "methyl imidazolium" should read -- methylimidazolium --
Column 14, line 5, reads "$SO_2(C_nF_{(2n+-x)}H_x)$" should read -- $SO_2(C_nF_{(2n+1-x)}H_x)$ --

Signed and Sealed this

Eleventh Day of March, 2008

JON W. DUDAS
*Director of the United States Patent and Trademark Office*